United States Patent
Rauer et al.

(10) Patent No.: US 8,084,740 B2
(45) Date of Patent: Dec. 27, 2011

(54) RADIOMETRIC MEASURING DEVICE WITH A TWO-WIRE SUPPLY

(75) Inventors: Winfried Rauer, Fischerbach (DE);
Josef Fehrenbach, Haslach (DE);
Thomas Deck, Wolfach (DE); Holger Sack, Schiltach (DE)

(73) Assignee: VEGA Grieshaber KG, Wolfach (DE)

( * ) Notice: Subject to any disclaimer, the term of this patent is extended or adjusted under 35 U.S.C. 154(b) by 0 days.

(21) Appl. No.: 12/714,891

(22) Filed: Mar. 1, 2010

(65) Prior Publication Data
US 2010/0230600 A1    Sep. 16, 2010

Related U.S. Application Data

(60) Provisional application No. 61/159,236, filed on Mar. 11, 2009.

(30) Foreign Application Priority Data

Mar. 11, 2009   (EP) .................................... 09 154 921

(51) Int. Cl.
*G01F 23/00* (2006.01)
(52) U.S. Cl. ..................................................... 250/357.1
(58) Field of Classification Search ............... 250/357.1, 250/395
See application file for complete search history.

(56) References Cited

U.S. PATENT DOCUMENTS

| | | | |
|---|---|---|---|
| 5,650,571 A * | 7/1997 | Freud et al. ................. | 73/861.06 |
| 6,014,100 A | 1/2000 | Fehrenbach et al. | |
| 7,018,800 B2 | 3/2006 | Huisenga et al. | |
| 7,280,048 B2 | 10/2007 | Longsdorf et al. | |
| 2002/0149379 A1* | 10/2002 | Rauer et al. ..................... | 324/678 |
| 2003/0213299 A1* | 11/2003 | Arndt .......................... | 73/290 V |
| 2004/0025569 A1* | 2/2004 | Damm et al. .................. | 73/32 R |
| 2004/0074295 A1* | 4/2004 | Michalski et al. ........... | 73/290 R |
| 2004/0128098 A1* | 7/2004 | Neuhaus et al. .............. | 702/122 |
| 2005/0075844 A1* | 4/2005 | Mueller et al. ................ | 702/189 |
| 2005/0116157 A1 | 6/2005 | Nistor | |
| 2007/0186678 A1 | 8/2007 | Griessbaum et al. | |
| 2007/0278404 A1 | 12/2007 | Spanke et al. | |

FOREIGN PATENT DOCUMENTS

| | | |
|---|---|---|
| DE | 44 07 369 | 9/1995 |
| DE | 100 48 559 | 4/2002 |
| DE | 10 2006 006 572 | 8/2007 |
| WO | 2006/104712 | 10/2006 |

* cited by examiner

*Primary Examiner* — David Porta
*Assistant Examiner* — Marcus Taningco
(74) *Attorney, Agent, or Firm* — Fay Kaplun & Marcin, LLP

(57) ABSTRACT

A measuring device with a two-wire supply for radiometric filling level measuring or density measuring of a feed material with a processor which is designed to change from an active mode to a power-saving mode.

14 Claims, 2 Drawing Sheets

US 8,084,740 B2

RADIOMETRIC MEASURING DEVICE WITH A TWO-WIRE SUPPLY

REFERENCE TO RELATED APPLICATIONS

This application claims the benefit of the filing date of European Patent Application Serial No. EP 09 154 921.2 filed 11 Mar. 2009 and United States Provisional Patent Application Ser. No. 61/159,236 filed 11 Mar. 2009, the disclosure of both applications is hereby incorporated by reference.

FIELD OF THE INVENTION

The invention relates to radiometric filling level measuring or density measuring of a feed material with a two-wire power supply (two-wire supply). In particular, the invention relates to a radiometric measuring device with a two-wire supply. Furthermore, the invention relates to a measuring system and a measuring method for radiometric filling level measuring or density measuring of a feed material with a two-wire supply.

BACKGROUND TO THE INVENTION

Radiometric measuring devices can be designed in four-wire technique, in which supply lines are separate from signal lines. In this arrangement it may be necessary to cable four lines to the device, which can result in considerable electricity consumption, considerable self-heating, and a high degree of switching effort.

Two-wire designs of radiometric measuring devices often only provide limited power.

SUMMARY OF THE INVENTION

The present invention relates to a measuring device, a measuring system and a measuring method for radiometric filling level measuring or density measuring of a feed material, i. e. a filling good, with a two-wire supply.

According to an exemplary embodiment of the invention, a measuring device with a two-wire supply for radiometric filling level measuring and/or density measuring of a feed material with a processor is provided, wherein the processor is designed to change from an active mode to a power-saving mode.

Such a measuring device, which may also be denoted as radiometric filling level measuring device and/or radiometric density measuring device, results in less energy consumption, less cabling effort, and the achievement of better measuring results due to less self-heating of the measuring device. With this measuring device it is possible to implement simpler and more economical circuits, wherein two-wire devices in models from 4 to 20 mA can be designed as a fieldbus device according to the Profibus (PA) standard or Foundation Fieldbus standard.

Furthermore, by means of such a measuring device in a two-wire design in which only limited power is available, by means of dynamic adjustment of the power consumption to the available power (power management) a reduction in the power consumption may be achieved.

According to an embodiment of the invention, the measuring device further comprises an energy storage unit, wherein the energy storage unit is designed to store energy and to capture or to store in the interim electric currents (i. e. electric energy) of components of the measuring device. The energy storage unit is furthermore designed to supply the measuring device with current.

According to a further exemplary embodiment of the invention, the energy storage unit is designed as an electrolytic power capacitor (Pufferelko). The energy storage unit can be designed as a capacitor, in particular as a double-layer capacitor.

According to a further exemplary embodiment of the invention, the measuring device comprises a signal amplifier and at least one comparator, wherein the processor for the power-saving mode is designed to switch off at least the signal amplifier or the at least one comparator. This means that the processor switches off either the signal amplifier or at least one comparator, or both the signal amplifier and the comparator.

Such a measuring device with a signal amplifier and comparator(s) that can be switched off may make it possible to reduce the power consumption by means of a power-saving design of the signal amplifier, Furthermore, the power consumption is reduced by the processor switching off the signal amplifier or the comparator if no measuring signal is present, because in this state no power is consumed by the signal amplifier or the comparator.

According to a further exemplary embodiment of the invention, the measuring device further comprises a switch, wherein the processor or some other control device is designed for (if need be automatic) controlling of the switch, and the switch regulates the energy supply of the at least one comparator and signal amplifier by way of the energy storage unit.

According to a further exemplary embodiment of the invention, the signal amplifier of the measuring device is designed for intermittent operation.

According to a further exemplary embodiment of the invention, the processor of the measuring device is designed for intermittent operation.

Such a processor of the measuring device, which is designed for intermittent operation, may make it possible for the processor to regulate power consumption of the measuring device depending on the presence of a measuring signal and thus to reduce the overall power consumption, for example by switching off the signal amplifier and/or the comparator(s) if no measuring signal is present.

According to a further exemplary embodiment of the invention, a measuring system is claimed for the radiometric measuring of a filling level or of a density of a feed material with a measuring device according to the above-mentioned exemplary embodiments and with a radioactive source.

Such a measuring system comprises a radioactive source and a radiometric sensor. The measuring system can be used as a level measuring system and/or density measuring system and is based on the scintillation principle. The radiometric sensor comprises a two-wire power pack, a processor, a high-voltage generating device by means of voltage multiplication, a scintillator, a photomultiplier, a signal amplifier and one or several comparator(s).

The scintillator converts the radiation (which can, for example, be gamma radiation or some other ionising radiation) to flashes of light, which are converted to current pulses by the photomultiplier such as a or 13 radiation. The subsequent signal amplifier amplifies the current pulses. Comparators convert the amplified current pulses to digital pulses that are counted by the processor. Depending on the process value, the intensity of the radiation that is radiated through the container or through the feed material changes, and thus the pulse rate changes.

From the pulse rate the processor determines the physical process value. In order to reduce power consumption, a power-saving processor is used that provides power-saving modes. This processor is activated as soon as a new measured value is present. If very little power is available, the signal amplifier and the comparator(s) are switched off. In order to collect the peak currents of the arranged components, energy-storage units such as electrolytic power capacitors are used, which are charged slowly and which can temporarily provide the required currents.

Such a measuring system may make it possible to reduce the power consumption in a two-wire design with limited power as a result of dynamic matching of the power consumption to the available power (power management), a current-saving design of the signal amplifier, a current-saving design of the high-voltage power pack of the photomultiplier by means of voltage multiplication, and as a result of intermittent operation of the amplifier and of the processor.

According to a further exemplary embodiment of the invention, a measuring method for radiometric measuring of the filling level or the density of a feed material by means of a measuring device with a two-wire supply is stated, in which a processor switches from an active mode to a current-saving mode for the purpose of saving power, and the processor is activated if a new measuring signal is present.

According to a further embodiment of the invention, a measuring method is stated which furthermore comprises the following steps: collection of currents by means of an energy storage unit; supply of current by way of the energy storage device.

According to a further exemplary embodiment of the invention, a measuring method is stated, which furthermore comprises the following steps: switching off a signal amplifier and at least one comparator by means of the processor for the power-saving mode. This means that either the signal amplifier or at least one of the comparators, or the signal amplifier and at least one of the comparators can be switched off.

According to a further embodiment of the invention, a measuring method is provided which furthermore comprises the following steps: intermittent operation of the signal amplifier; intermittent operation of the processor.

According to a further exemplary embodiment of the invention, a program element is stated which when executed on a processor of a measuring device (100) with a two-wire supply (101) for radiometric measuring of the filling level or the density of a feed material directs the processor to carry out the following steps: switching a processor from an active mode to a power-saving mode for saving power, and activating the processor when a new measuring signal is present. Furthermore, the following steps can be provided: switching off a signal amplifier and at least one comparator by means of the processor for the power-saving mode; intermittent operation of the signal amplifier; intermittent operation of the processor.

According to a further exemplary embodiment of the invention, a computer-readable medium is claimed, on which a program element is stored which when executed on a processor of a measuring device (100) with a two-wire supply (101) for radiometric measuring of the filling level or the density of a feed material directs the processor to carry out the following steps: switching a processor from an active mode to a power-saving mode for saving power, and activating the processor when a new measuring signal is present. Furthermore, the following steps can be provided: switching off a signal amplifier and at least one comparator by means of the processor for the power-saving mode; intermittent operation of the signal amplifier; intermittent operation of the processor.

The individual characteristics of the different exemplary embodiments can of course also be combined, which may in part also result in advantageous effects that exceed the sum of individual effects even if they are not expressly described.

It should, in particular, be noted that the characteristics described above and below with reference to the measuring device and/or to the measuring system are also implementable in the method, the program element and the computer-readable medium, and vice versa.

These and other aspects of the invention are explained and clarified with reference to the exemplary embodiments described below.

DETAILED DESCRIPTION OF EXEMPLARY EMBODIMENTS

Figure 1:
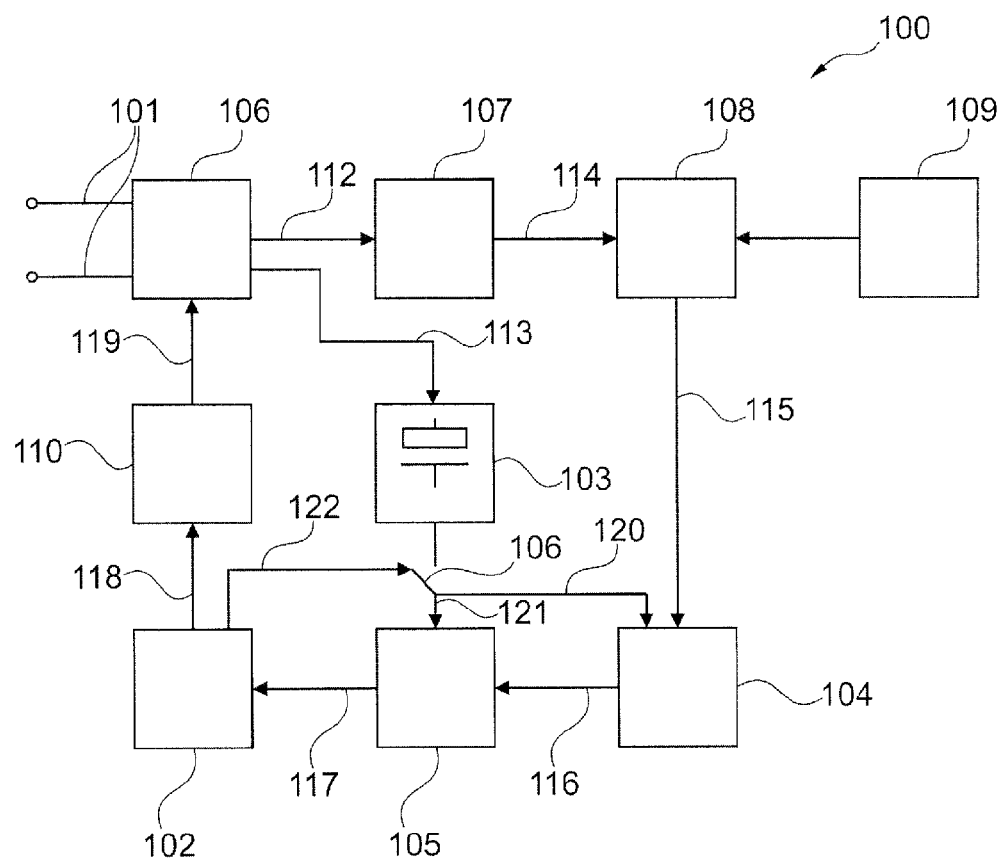
FIG. 1 shows a diagrammatic view of a radiometric measuring device with a two-wire supply, according to an exemplary embodiment of the invention.

Below, exemplary embodiments of the invention are described with reference to the enclosed drawings.

The illustrations in the figures are diagrammatic and not to scale. In the following description of the figures the same reference characters are used for identical or similar elements.

FIG. 1 shows a measuring device 100 with a two-wire supply 101 for radiometric filling level measuring or density measuring of a feed material. The measuring device 100 can be designated a radiometric sensor. The two-wire supply 101 supplies a power pack 106 that by way of a line 112 supplies a high-voltage generating unit 107 and by way of a line 113 supplies an energy storage unit 103 that can be designed as an electrolytic power capacitor. The high-voltage generating unit 107 generates high voltage, for example by means of voltage multiplication. The high-voltage generating unit 107 supplies high voltage to a photomultiplier 108 by way of a line 114.

A scintillator 109 converts radioactive gamma radiation into flashes of light that are transmitted to the photomultiplier 108 that converts the flashes of light to current pulses. The current pulses are transmitted from the photomultiplier 108 to a signal amplifier 104 by way of a line 115. The signal amplifier 104 amplifies the current pulses and forwards the current pulses by way of a line 116 to at least one comparator 105 that converts the current pulses to digital pulses. The comparator 105 guides the digital pulses to a processor 102 by way of a line 117. The processor 102 counts the pulses.

Depending on the process value, the radioactive field and thus the pulse rate change. The processor 102 determines the physical process value from the pulse rate and forwards it by way of a line 118 to a current output interface or fieldbus interface 110. The fieldbus interface 110 is designed as a 4 to 20 mA circuit or according to the Profibus standard or Foundation Fieldbus standard. The fieldbus interface 110 transmits the physical process value by way of a line 119 to the power pack 106 that transmits the process value by way of one of the lines 101 of the two-wire supply 101 to an evaluation unit (not shown in FIG. 1).

The energy storage unit 103 supplies the signal amplifier 104 with current or electrical power by way of a switch 106 and a line 120, and supplies the comparator 105 by way of the switch 106 and a line 121. By way of a line 122 the processor 102 controls the switch 106 that regulates the energy supply of the at least one comparator 105 and of the signal amplifier 104 by way of the energy storage unit 103.

Figure 2:
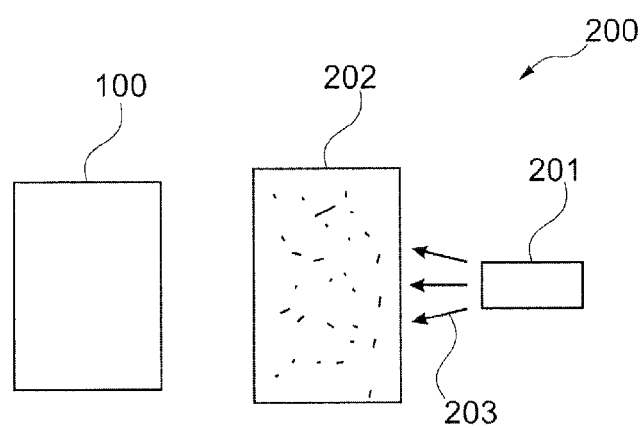
FIG. 2 shows a diagrammatic view of a radiometric measuring system with a two-wire supply, according to an exemplary embodiment of the invention.

FIG. 2 shows a radiometric measuring system 200 with a two-wire supply for radiometric filling level measuring or density measuring of a feed material with a measuring device 100 and a radioactive source 201. The radioactive source 201 transmits, for example, radioactive gamma radiation 203 onto a feed material container 202, which comprises, for example, a bulk material or a liquid, wherein the radioactive rays, having penetrated the feed material container 202 or the liquid or the bulk material of the feed material container 202, are received by the measuring device 100 and is converted to a measured value.

Figure 3:
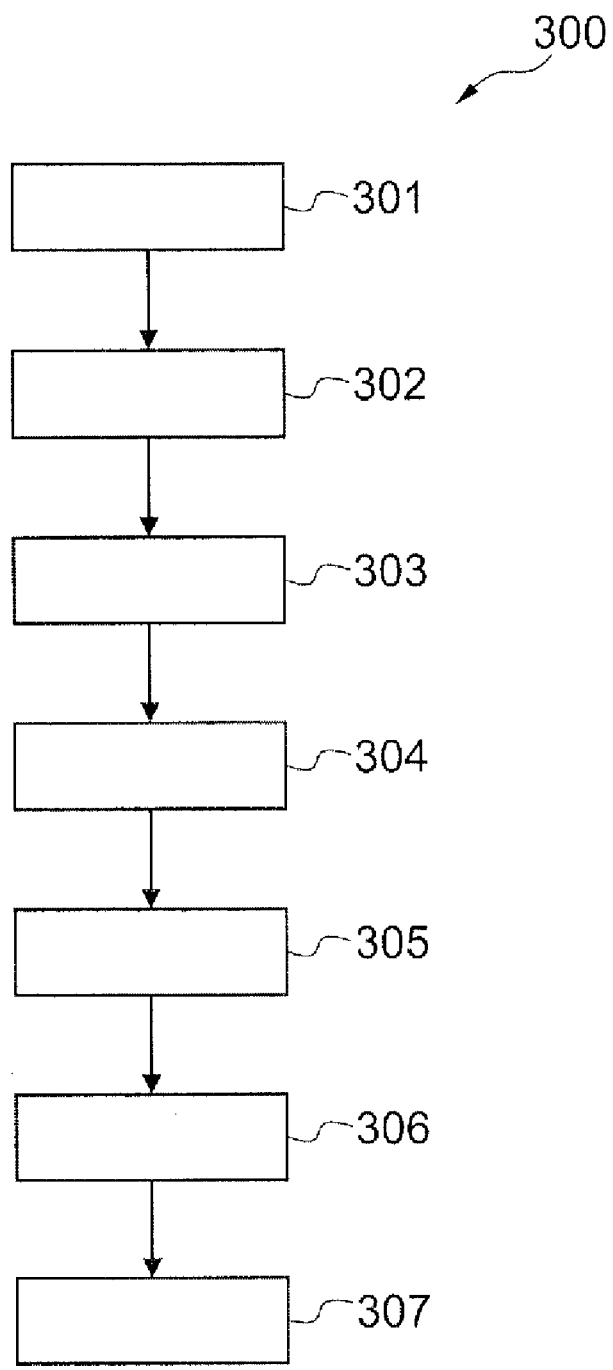
FIG. 3 shows a flow chart of a radiometric measuring method with a two-wire supply, according to an exemplary embodiment of the invention.

FIG. 3 shows a radiometric measuring method 300 for radiometric measuring of the filling level or the density of a feed material by means of a measuring device 100 with a two-wire supply 101, with said measuring method 300 comprising the following steps: switching a processor 102 from an active mode to a power-saving mode for saving power (step 301); activating the processor 102 when a new measuring signal is present (step 302); collecting currents by means of an energy storage unit 103 (step 303); supplying power by means of the energy storage unit 103 (step 304); switching off a signal amplifier 104 and at least one comparator 105 by means of the processor 102 for the power-saving mode (step 305); intermittent operation of the signal amplifier 104 (step 306); and intermittent operation of the processor 102 (step 307).

Although the invention was described with reference to exemplary embodiments, various alterations and modifications can be carried out without leaving the scope of protection of the invention. The invention can also be used in fields other than in filling level measuring or density measuring with any radiometric measuring with a two-wire supply.

In addition, it should be pointed out that "comprising" does not exclude other elements or steps, and "a" or "one" does not exclude a plural number. In particular, the measuring device can thus, for example, comprise more than one processor, more than one energy storage unit, more than one signal amplifier, more than one comparator, or several switches. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

The invention claimed is:

1. A measuring device for radiometric measuring of one of a filling level and a density of a feed material, comprising:
   a two-wire supply; and
   a processor configured to change from an active mode to a power-saving mode,
   wherein the processor is activated as soon as a new measurement value is present.

2. The measuring device according to claim 1, further comprising:
   an energy storage unit storing energy, the energy storage unit collecting currents of components of the measuring device and supplying the measuring device with current.

3. The measuring device according to claim 2, wherein the energy storage unit is an electrolytic power capacitor.

4. The measuring device according to claim 1, further comprising:
   a signal amplifier; and
   a comparator,
   wherein the processor switches off at least one of the signal amplifier and the comparator.

5. The measuring device according to claim 4, further comprising:
   a switch regulating the energy supply of at least one of the comparator and the signal amplifier using the energy storage unit, the switch being controlled by the processor.

6. The measuring device according to claim 4, wherein the signal amplifier is configured for an intermittent operation.

7. The measuring device according to claim 1, wherein the processor is configured for an intermittent operation.

8. A measuring system for the radiometric measuring of one of a filling level and a density of a feed material, comprising:
   a two-wire supply;
   a processor configured to change from an active mode to a power-saving mode; and
   a radioactive source arrangement,
   wherein the processor is activated as soon as a new measurement value is present.

9. A measuring method for a radiometric measuring of one of a filling level and a density of a feed material using a measuring device with a two-wire supply, comprising:
   switching a processor of the measuring device from an active mode to a power-saving mode for saving power; and
   activating the processor if a new measurement value is present.

10. A measuring method according to claim 9, further comprising:
    collecting currents using an energy storage unit of the measuring device; and
    supplying the power using the energy storage unit.

11. The measuring method according to claim 9, further comprising:
    switching off at least one of a signal amplifier of the measuring device and a comparator of the measuring device using the processor for the power-saving mode.

12. The measuring method according to claim 9, further comprising:
    performing an intermittent operation of a signal amplifier of the measuring device; and
    performing an intermittent operation of the processor.

13. A program embodied on a non-transitory computer readable medium executable by a processor of a measuring device with a two-wire supply for radiometric measuring of one of a filling level and a density of a feed material directs the processor to carry out the following steps:
    switching a processor from an active mode to a power-saving mode for saving power; and
    activating the processor when a new measurement value is present.

14. A non-transitory computer-readable medium on which a program element is stored which when executed on a processor of a measuring device with a two-wire supply for radiometric measuring of one of a filling level and a density of a feed material directs the processor to carry out the following steps:
    switching a processor from an active mode to a power-saving mode for saving power; and
    activating the processor when a new measurement value is present.

* * * * *